US005684129A

United States Patent [19]

Fish

[11] Patent Number: 5,684,129

[45] Date of Patent: Nov. 4, 1997

[54] INTERFERON RECEPTOR BINDING PEPTIDES

[76] Inventor: Eleanor N. Fish, 20 Loganberry Crescent, North York, Ontario, Canada, M2H 3H1

[21] Appl. No.: 362,453

[22] PCT Filed: Jul. 6, 1993

[86] PCT No.: PCT/CA93/00279

§ 371 Date: Mar. 10, 1995

§ 102(e) Date: Mar. 10, 1995

[87] PCT Pub. No.: WO94/01457

PCT Pub. Date: Jan. 20, 1994

Related U.S. Application Data

[63] Continuation of Ser. No. 980,525, Nov. 20, 1992, abandoned, which is a continuation of Ser. No. 909,739, Jul. 7, 1992, abandoned.

[51] Int. Cl.$^6$ .............................. A61K 38/00; C07K 7/06; C07K 7/08

[52] U.S. Cl. .............................. 530/326; 530/327; 530/328

[58] Field of Search .............................. 514/13; 530/327, 530/326

[56] References Cited

PUBLICATIONS

Zav'yyalov, V.P., Denesyuk, A.I.; *Immunol.Lett.* 4:7–14, 1982.

Meister, A., Uze, G., Mogensen, K.E., Gresser, I., Tovey, M.G., Grutter, M., Meyer, F.; *J. Gen. Virol.* 67; 1633–1643, 1987; p.1641.

Marcucci, F., De Maeyer, E.; *Biochem. Biophys. Res. Commun.* 134: 1412–1418, 1986; p. 1417.

Fish, E.N., Banerjee, K., Stebbing, N. *J. IFN Res.* 9:97–114, 1989.

Senda, T., Matsuda, S., Kurihara, H., Nakamura, K.T., Kawano, G., Shimizu, H., Mizuno, H., Mitsui, Y.; *Proc. Japan Acad.* 66:77–80, 1990.

Fish, E.N. *J. IFN Res.* 12:257–266, 1992.

Shafferman, A., Velan, B., Cohen, S., Leitner, M., Grosfeld, H.J. *Biol. Chem.* 262: 6227–6237, 1987.

Raj, N.B.K., Israeli, R., Kelley, K.A., Leach, S.J., Minasian, E., Sikaris,K., Parry, D.A.D., Pitha, P.M.: *J.Bio. Chem..* 263:8943–8952, 1988.

Zav'yalov, V.P.; Denesyuk, A.I., Aav'yalova, G.A.; *Immunol. Lett.* 22:173–182, 1989.

Branca et al, Nature, 294, pp. 768–770, (1981).

Bazan, *Proc. Natl. Acad. Sci.,* 87: 6934–6938, (1990).

Anderson, et al, J. Biol. Chem. 257, pp. 11301–11304 (1982).

Hannigan et al, EMBRO J. vol. 5, pp. 1607–1613 (1986).

*Primary Examiner*—Cecilia J. Tsang
*Assistant Examiner*—S. G. Marshall
*Attorney, Agent, or Firm*—Nikaido Marmelstein Murray & Oram LLP

[57] ABSTRACT

A polypeptide for use as an interferon receptor-binding peptide, said polypeptide selected from the group of peptides having an amino acid sequence substantially of the formulae; CYS-LEU-LYS-ASP-ARG-HIS-ASP; ASP-GLU-SER-LEU-LEU-GLU-LYS-PHE-TYR-THR-GLU-LEU-TYR-GLN-LEU-ASN-ASP; ASN-GLU-THR-ILE-VAL-GLU-ASN-LEU-LEU-ALA-ASN-VAL-TYR-HIS-GLN-ILE-ASN-HIS; TYR-LEU-THR-GLU-LYS-LYS-TYR-SER-PRO-CYS-ALA; TYR-PHE-GLN-ARG-ILE-THR-LEU-TYR-LEU-THR-GLU-LYS-LYS-TYR-SER-PRO-CYS-ALA; TYR-PHE-GLN-ARG-ILE-THR-LEU-TYR; and GLU-LEU-TYR-GLN-GLN-LEU-ASN-ASP. The polypeptides are useful for delivering a pharmaceutically active drug to a cell.

8 Claims, 9 Drawing Sheets

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 7 amino acids
( B ) TYPE: amino acid
( D ) TOPOLOGY: unknown ( i i ) MOLECULE TYPE: peptide ( x i ) SEQUENCE DESCRIPTION: SEQ ID NO:1:

```
Cys Leu Lys Asp Arg His Asp
1               5
```

( 2 ) INFORMATION FOR SEQ ID NO:2:

( i ) SEQUENCE CHARACTERISTICS:
( A ) LENGTH: 18 amino acids
( B ) TYPE: amino acid
( D ) TOPOLOGY: unknown ( i i ) MOLECULE TYPE: peptide ( x i ) SEQUENCE DESCRIPTION: SEQ ID NO:2:

```
Asp Glu Ser Leu Leu Glu Lys Phe Tyr Thr Glu Leu Tyr Gln Gln Leu
1               5                   10                  15

Asn Asp
```

( 2 ) INFORMATION FOR SEQ ID NO:3:

( i ) SEQUENCE CHARACTERISTICS:
( A ) LENGTH: 18 amino acids
( B ) TYPE: amino acid
( D ) TOPOLOGY: unknown ( i i ) MOLECULE TYPE: peptide ( x i ) SEQUENCE DESCRIPTION: SEQ ID NO:3:

```
Asn Glu Thr Ile Val Glu Asn Leu Leu Ala Asn Val Tyr His Gln Ile
1               5                   10                  15

Asn His
```

( 2 ) INFORMATION FOR SEQ ID NO:4:

( i ) SEQUENCE CHARACTERISTICS:
( A ) LENGTH: 11 amino acids
( B ) TYPE: amino acid
( D ) TOPOLOGY: unknown ( i i ) MOLECULE TYPE: peptide ( x i ) SEQUENCE DESCRIPTION: SEQ ID NO:4:

Tyr Leu Thr Glu Lys Lys Tyr Ser Pro Cys Ala
1 5 10

( 2 ) INFORMATION FOR SEQ ID NO:5:

( i ) SEQUENCE CHARACTERISTICS:
( A ) LENGTH: 18 amino acids
( B ) TYPE: amino acid
( D ) TOPOLOGY: unknown ( i i ) MOLECULE TYPE: peptide ( x i ) SEQUENCE DESCRIPTION: SEQ ID NO:5:

Tyr Phe Gln Arg Ile Thr Leu Tyr Leu Thr Glu Lys Lys Tyr Ser Pro
1 5 10 15

Cys Ala ( 2 ) INFORMATION FOR SEQ ID NO:6:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( x i ) SEQUENCE DESCRIPTION: SEQ ID NO:6:

Tyr Phe Gln Arg Ile Thr Leu Tyr
1 5

( 2 ) INFORMATION FOR SEQ ID NO:7:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: peptide ( x i ) SEQUENCE DESCRIPTION: SEQ ID NO:7:

Glu Leu Tyr Gln Gln Leu Asn Asp
1 5

( 2 ) INFORMATION FOR SEQ ID NO:8:

( i ) SEQUENCE CHARACTERISTICS:
( A ) LENGTH: 166 amino acids
( B ) TYPE: amino acid
( D ) TOPOLOGY: unknown ( i i ) MOLECULE TYPE: protein ( x i ) SEQUENCE DESCRIPTION: SEQ ID NO:8:

Cys Asp Leu Pro Gln Thr His Ser Leu Gly Asn Arg Arg Thr Leu Ile
1 5 10 15

Leu Leu Ala Gln Met Arg Arg Ile Ser Pro Phe Ser Cys Leu Lys Asp
20 25 30

-continued

Arg His Asp Phe Gly Phe Pro Gln Glu Glu Phe Asp Gly Asn Gln Phe
35 40 45

Gln Lys Ala Gln Ala Ile Ser Tyr Leu His Glu Met Ile Gln Gln Thr
50 55 60

Phe Asn Leu Phe Ser Thr Lys Asp Ser Ser Ala Ala Trp Asp Glu Ser
65 70 75 80

Leu Leu Glu Lys Phe Tyr Thr Glu Leu Tyr Gln Gln Leu Asn Asp Leu
85 90 95

Glu Ala Cys Tyr Ile Gln Glu Val Gly Val Glu Glu Thr Pro Leu Met
100 105 110

Asn Val Asp Ser Ile Leu Ala Val Arg Lys Tyr Phe Gln Arg Ile Thr
115 120 125

Leu Tyr Leu Thr Glu Lys Lys Tyr Ser Pro Cys Ala Trp Glu Val Val
130 135 140

Arg Ala Glu Ile Met Arg Ser Phe Ser Leu Ser Thr Asn Leu Gln Glu
145 150 155 160

Arg Leu Arg Arg Lys Glu
165

( 2 ) INFORMATION FOR SEQ ID NO:9:

( i ) SEQUENCE CHARACTERISTICS:
( A ) LENGTH: 166 amino acids
( B ) TYPE: amino acid
( D ) TOPOLOGY: unknown ( i i ) MOLECULE TYPE: protein ( x i ) SEQUENCE DESCRIPTION: SEQ ID NO:9:

Cys Asp Leu Pro Gln Thr His Ser Leu Gly Ser Arg Arg Thr Leu Met
1 5 10 15

Leu Leu Ala Gln Met Arg Arg Ile Ser Leu Phe Ser Cys Leu Lys Asp
20 25 30

Arg His Asp Phe Gly Phe Pro Gln Glu Glu Phe Xaa Gly Asn Gln Phe
35 40 45

Gln Lys Ala Glu Thr Ile Pro Val Leu His Glu Met Ile Gln Gln Ile
50 55 60

Phe Asn Leu Phe Ser Thr Lys Asp Ser Ser Ala Ala Trp Asp Glu Thr
65 70 75 80

Leu Leu Asp Lys Phe Tyr Thr Glu Leu Tyr Gln Gln Leu Asn Asp Leu
85 90 95

Glu Ala Cys Tyr Ile Gln Gly Val Gly Val Thr Glu Thr Pro Leu Met
100 105 110

Lys Glu Asp Ser Ile Leu Ala Val Arg Lys Tyr Phe Gln Arg Ile Thr
115 120 125

Leu Tyr Leu Thr Glu Lys Lys Tyr Ser Pro Cys Ala Trp Glu Val Val
130 135 140

Arg Ala Glu Ile Met Arg Ser Phe Ser Leu Ser Thr Asn Leu Gln Glu
145 150 155 160

Ser Leu Arg Ser Lys Glu
165

( 2 ) INFORMATION FOR SEQ ID NO:10:

( i ) SEQUENCE CHARACTERISTICS:
( A ) LENGTH: 150 amino acids
( B ) TYPE: amino acid
( D ) TOPOLOGY: unknown ( i i ) MOLECULE TYPE: protein ( x i ) SEQUENCE DESCRIPTION: SEQ ID NO:10:

Gln Thr His Ser Leu Gly Ser Arg Arg Thr Leu Met Leu Leu Ala Gln
1 5 10 15

Met Arg Arg Ile Ser Leu Phe Ser Cys Leu Lys Asp Arg His Asp Phe
20 25 30

Gly Phe Pro Gln Glu Glu Phe Gly Asn Gln Phe Gln Lys Ala Glu Thr
35 40 45

Ile Pro Val Leu His Glu Met Ile Gln Gln Ile Phe Asn Leu Phe Ser
50 55 60

Thr Lys Asp Ser Ser Ala Ala Trp Asp Glu Thr Leu Leu Asp Lys Phe
65 70 75 80

Tyr Thr Glu Leu Tyr Gln Gln Leu Asn Asp Leu Glu Ala Cys Tyr Ile
85 90 95

Gln Gly Val Gly Val Thr Glu Thr Pro Leu Met Lys Glu Asp Ser Ile
100 105 110

Leu Ala Val Arg Lys Tyr Phe Gln Arg Ile Thr Leu Tyr Leu Thr Glu
115 120 125

Lys Lys Tyr Ser Pro Cys Ala Trp Glu Val Val Arg Ala Glu Ile Met
130 135 140

Arg Ser Phe Ser Leu Ser
145 150

( 2 ) INFORMATION FOR SEQ ID NO:11:

( i ) SEQUENCE CHARACTERISTICS:
( A ) LENGTH: 150 amino acids
( B ) TYPE: amino acid
( D ) TOPOLOGY: unknown ( i i ) MOLECULE TYPE: protein ( x i ) SEQUENCE DESCRIPTION: SEQ ID NO:11:

Gln Thr His Ser Leu Gly Ser Arg Arg Thr Leu Met Leu Leu Ala Gln
1 5 10 15

Met Arg Arg Ile Ser Leu Phe Ser Cys Leu Lys Asp Arg His Asp Phe
20 25 30

Gly Phe Pro Gln Glu Glu Phe Gly Asn Gln Phe Gln Lys Ala Glu Thr
35 40 45

Ile Pro Val Leu His Glu Met Ile Gln Gln Ile Phe Asn Leu Phe Ser
50 55 60

Thr Lys Asp Ser Ser Ala Ala Trp Asp Glu Thr Leu Leu Asp Lys Phe
65 70 75 80

Tyr Thr Glu Leu Tyr Gln Gln Leu Asn Asp Leu Glu Ala Cys Tyr Ile
85 90 95

Gln Gly Val Gly Val Thr Glu Thr Pro Leu Met Lys Glu Asp Ser Ile
100 105 110

Leu Ala Val Arg Lys Tyr Phe Gln Arg Ile Thr Leu Tyr Leu Thr Glu
115 120 125

Lys Lys Tyr Ser Pro Cys Ala Trp Glu Val Val Arg Ala Glu Ile Met
130 135 140

Arg Ser Phe Ser Leu Ser
145 150

( 2 ) INFORMATION FOR SEQ ID NO:12:

-continued ( i ) SEQUENCE CHARACTERISTICS:
( A ) LENGTH: 150 amino acids
( B ) TYPE: amino acid
( D ) TOPOLOGY: unknown ( i i ) MOLECULE TYPE: protein ( x i ) SEQUENCE DESCRIPTION: SEQ ID NO:12:

```
Gln Thr His Ser Leu Gly Ser Arg Arg Thr Leu Met Leu Leu Ala Gln
1               5                   10                  15

Met Arg Arg Ile Ser Leu Phe Ser Cys Leu Lys Asp Arg His Asp Phe
            20                  25                  30

Gly Phe Pro Gln Glu Glu Phe Gly Asn Gln Phe Gln Lys Ala Glu Thr
        35                  40                  45

Ile Pro Val Leu His Glu Met Ile Gln Gln Ile Phe Asn Leu Phe Ser
    50                  55                  60

Thr Lys Asp Ser Ser Ala Ala Trp Asp Glu Thr Leu Leu Asp Lys Phe
65                  70                  75                  80

Tyr Thr Glu Leu Tyr Gln Gln Leu Asn Asp Leu Glu Ala Cys Tyr Ile
                85                  90                  95

Gln Gly Val Gly Val Thr Glu Thr Pro Leu Met Lys Glu Asp Ser Ile
            100                 105                 110

Leu Ala Val Arg Lys Tyr Phe Gln Arg Ile Thr Leu Tyr Leu Thr Glu
        115                 120                 125

Lys Lys Tyr Ser Pro Cys Ala Trp Glu Val Val Arg Ala Glu Ile Met
    130                 135                 140

Arg Ser Phe Ser Leu Ser
145                 150
```

( 2 ) INFORMATION FOR SEQ ID NO:13:

( i ) SEQUENCE CHARACTERISTICS:
( A ) LENGTH: 165 amino acids
( B ) TYPE: amino acid
( D ) TOPOLOGY: unknown ( i i ) MOLECULE TYPE: protein ( x i ) SEQUENCE DESCRIPTION: SEQ ID NO:13:

```
Cys Asp Leu Pro Glu Thr His Ser Leu Gly Ser Arg Arg Thr Leu Met
1               5                   10                  15

Leu Leu Ala Gln Met Arg Arg Ile Ser Leu Ser Ser Cys Leu Met Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Leu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Tyr Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Thr Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160
```

-continued

Leu Arg Ser Lys Glu
165

( 2 ) INFORMATION FOR SEQ ID NO:14:

( i ) SEQUENCE CHARACTERISTICS:
( A ) LENGTH: 165 amino acids
( B ) TYPE: amino acid
( D ) TOPOLOGY: unknown ( i i ) MOLECULE TYPE: protein ( x i ) SEQUENCE DESCRIPTION: SEQ ID NO:14:

Cys Asp Leu Pro Glu Thr His Ser Leu Gly Ser Arg Arg Thr Leu Met
1 5 10 15

Leu Leu Ala Gln Met Arg Arg Ile Ser Leu Phe Ser Cys Ala Lys Ala
20 25 30

Ala His Asp Phe Gly Phe Pro Gln Glu Glu Phe Gly Asn Gln Phe Gln
35 40 45

Lys Ala Glu Thr Ile Pro Val Leu His Leu Met Ile Gln Gln Ile Phe
50 55 60

Asn Leu Phe Ser Thr Lys Asp Ser Ser Ala Ala Trp Asp Glu Thr Leu
65 70 75 80

Leu Asp Lys Phe Tyr Thr Glu Leu Tyr Gln Gln Leu Asn Asp Leu Glu
85 90 95

Ala Cys Tyr Ile Gln Gly Val Gly Val Thr Glu Thr Pro Leu Met Lys
100 105 110

Glu Asp Ser Ile Leu Ala Val Arg Lys Tyr Phe Gln Arg Ile Thr Leu
115 120 125

Tyr Leu Thr Glu Lys Lys Tyr Ser Pro Cys Ala Trp Glu Val Val Arg
130 135 140

Ala Glu Ile Met Arg Ser Phe Ser Leu Ser Thr Asn Leu Gln Glu Ser
145 150 155 160

Leu Arg Ser Lys Glu
165

( 2 ) INFORMATION FOR SEQ ID NO:15:

( i ) SEQUENCE CHARACTERISTICS:
( A ) LENGTH: 162 amino acids
( B ) TYPE: amino acid
( D ) TOPOLOGY: unknown ( i i ) MOLECULE TYPE: protein ( x i ) SEQUENCE DESCRIPTION: SEQ ID NO:15:

Glu Thr His Ser Leu Asp Asn Arg Arg Thr Leu Met Leu Leu Ala Gln
1 5 10 15

Met Ser Arg Ile Ser Pro Ser Ser Cys Leu Met Asp Arg His Asp Phe
20 25 30

Gly Phe Pro Gln Glu Glu Phe Asp Gly Asn Gln Phe Gln Lys Ala Pro
35 40 45

Ala Ile Ser Val His Leu Glu Leu Ile Gln Gln Ile Phe Asn Leu Phe
50 55 60

Thr Thr Lys Asp Ser Ser Ala Ala Trp Asp Glu Asp Leu Leu Asp Lys
65 70 75 80

Phe Cys Thr Glu Leu Tyr Gln Gln Leu Asn Asp Leu Glu Ala Cys Tyr
85 90 95

Met Gln Glu Glu Arg Val Gly Glu Thr Pro Leu Met Asn Ala Asp Ser

-continued 100 105 110

Ile Leu Ala Val Lys Lys Tyr Phe Arg Arg Ile Thr Leu Tyr Leu Thr
115 120 125

Glu Lys Lys Tyr Ser Pro Cys Ala Trp Glu Val Val Arg Ala Glu Ile
130 135 140

Met Arg Ser Phe Ser Leu Ser Thr Asn Leu Gln Glu Arg Leu Arg Arg
145 150 155 160

Lys Glu ( 2 ) INFORMATION FOR SEQ ID NO:16:

( i ) SEQUENCE CHARACTERISTICS:
( A ) LENGTH: 166 amino acids
( B ) TYPE: amino acid
( D ) TOPOLOGY: unknown ( i i ) MOLECULE TYPE: protein ( x i ) SEQUENCE DESCRIPTION: SEQ ID NO:16:

Met Ser Tyr Asn Leu Leu Gly Phe Leu Gln Arg Ser Ser Asn Phe Gln
1 5 10 15

Cys Gln Lys Leu Leu Trp Gln Leu Asn Gly Arg Leu Glu Tyr Cys Leu
20 25 30

Lys Asp Arg Met Asn Phe Asp Ile Pro Glu Glu Glu Lys Gln Leu Gln
35 40 45

Gln Phe Gln Lys Glu Asp Ala Ala Leu Thr Ile Tyr Glu Met Leu Gln
50 55 60

Asn Ile Phe Ala Ile Phe Arg Gln Asp Ser Ser Ser Thr Gly Trp Asn
65 70 75 80

Glu Thr Ile Val Glu Asn Leu Leu Ala Asn Val Val His Gln Asn His
85 90 95

Leu Lys Thr Val Leu Glu Glu Lys Leu Glu Lys Glu Asp Phe Thr Phe
100 105 110

Ile Gly Lys Leu Met Ser Ser Leu His Leu Lys Arg Tyr Tyr Gly Arg
115 120 125

Ile Leu His Tyr Leu Lys Ala Lys Glu Tyr Ser His Cys Ala Trp Thr
130 135 140

Ile Val Ala Val Glu Ile Leu Arg Asn Phe Tyr Leu Ile Asn Arg Leu
145 150 155 160

Thr Gly Tyr Leu Arg Asn
165

( 2 ) INFORMATION FOR SEQ ID NO:17:

( i ) SEQUENCE CHARACTERISTICS:
( A ) LENGTH: 168 amino acids
( B ) TYPE: amino acid
( D ) TOPOLOGY: unknown ( i i ) MOLECULE TYPE: protein ( x i ) SEQUENCE DESCRIPTION: SEQ ID NO:17:

Cys Asp Leu Pro Gln Thr His Asn Leu Arg Asn Lys Arg Ala Leu Thr
1 5 10 15

Leu Leu Val Gln Met Arg Arg Leu Ser Pro Leu Ser Cys Leu Lys Asp
20 25 30

Arg Lys Asp Phe Gly Phe Pro Gln Glu Lys Val Asp Ala Gln Gln Ile
35 40 45

Gln Lys Ala Gln Ala Ile Pro Val Leu Ser Glu Leu Thr Gln Gln Ile

-continued

| | | | | | | | | | | | | | | | |
|---|---|---|---|---|---|---|---|---|---|---|---|---|---|---|---|
| | 50 | | | | | 55 | | | | | 60 | | | | |
| Leu | Asn | Ile | Phe | Thr | Ser | Lys | Asp | Ser | Ser | Ala | Ala | Trp | Asn | Ala | Thr |
| 65 | | | | | 70 | | | | | 75 | | | | | 80 |
| Leu | Leu | Asp | Ser | Phe | Cys | Asn | Asp | Leu | His | Gln | Cys | Leu | Asn | Asp | Leu |
| | | | | 85 | | | | | 90 | | | | | 95 | |
| Gln | Ala | Cys | Leu | Met | Gln | Glu | Val | Gly | Val | Gln | Glu | Pro | Pro | Leu | Thr |
| | | | 100 | | | | | 105 | | | | | 110 | | |
| Gln | Glu | Asp | Ser | Leu | Leu | Ala | Val | Arg | Lys | Tyr | Phe | His | Arg | Ile | Thr |
| | | 115 | | | | | 120 | | | | | 125 | | | |
| Val | Val | Leu | Arg | Glu | Lys | Lys | His | Ser | Pro | Cys | Ala | Trp | Glu | Val | Val |
| | 130 | | | | | 135 | | | | | 140 | | | | |
| Arg | Ala | Glu | Val | Val | Val | Arg | Ala | Leu | Ser | Ser | Ser | Ala | Asn | Leu | Leu |
| 145 | | | | | 150 | | | | | 155 | | | | | 160 |
| Ala | Arg | Leu | Ser | Glu | Glu | Lys | Glu | | | | | | | | |
| | | | | 165 | | | | | | | | | | | |

INTERFERON RECEPTOR BINDING PEPTIDES

This application is a 371 of PCT/CA93/00279 filed Jul. 06, 1993 which is a continuation of Ser. No. 07/980,525 filed Nov. 20, 1992, now abandoned, which is a continuation of Ser. No. 07/909,739, filed Jul. 7, 1992, now abandoned.

BACKGROUND OF THE INVENTION

This invention relates generally to receptor binding domains in proteins and more specifically, to specific peptides that interact with the Type 1 human interferon receptor complex.

In order for any pharmaceutical composition to be therapeutically effective, it must be formulated in such a way that it reaches the desired target cells intact. Moreover, once at the site of action, the therapeutic must specifically interact with the target cells. Thus, the design and development of suitable carrier molecules, that may themselves be inert or active, allows for effective targeting of clinically active drugs. Much work has been done in the field of carriers for pharmaceutical compositions. Most recently, peptides have been identified as potentially suitable carriers for pharmaceutical compositions.

The interferons (hereinafter referred to as IFNs) are a family of biologically active proteins that are classified into three major groups, namely, IFN-alpha, IFN-beta and IFN-gamma. IFNs affect a wide variety of cellular functions, related to cell growth control, the regulation of immune responses and more specifically, the induction of antiviral responses. The ability of IFNs to modulate cell growth is observed with many cell types and is particularly effective in the case of tumor cells, which has led to the widespread interest in the use of IFNs for the treatment of neoplaslias.

The presence of a specific receptor at the cell surface is the first requirement for IFN action. Cells that lack these specific receptors are resistant to the effects of IFN. Receptor binding studies have identified the existence of at least two functional IFN receptors that are integral parts of the cell membrane on human cells. Branca, A. A. and Baglioni, C., (1981) *Nature* 294, 768–770 report that IFN-alpha and IFN-beta bind to one type of receptor and Anderson, P. et al, (1982) *J. Biol. Chem.* 257, 11301–11304 report that IFN-gamma binds to a separate receptor. IFN receptors are ubiquitous and more specifically, are upregulated in metabolically active cells such as cancer cells and infected tissues. Although several of the effects of IFNs such as the antiviral state, take several hours to develop, signal transduction immediately following the binding of IFN to its receptor is a rapid event. Since metabolic changes, such as increases in the transcriptional rate of some IFN-induced genes can be detected within five minutes of the addition of IFN, at least some of the transmembrane signals must be very rapid. Hannigan et al, (1986) *EMBO J.* 5, 1607–1613 suggest that receptor occupancy modulates the transcriptional response of specific genes to IFN. Indeed, there is accumulating evidence to suggest that there is a direct relationship between the number of receptors occupied and the amount of signal that is transduced to the cell nucleus. These transduced signals result in altered gene expression in the nucleus, which mediates the subsequent biological responses.

Extensive studies were undertaken to define those critical clusters of amino acids in the different IFN-alphas and IFN-beta that interact with the Type 1 IFN receptor complex. It is thought that these critical peptide domains would serve as prototypes for synthetic peptides that are useful as carriers for pharmaceutical compositions.

SUMMARY OF THE INVENTION

Thus, the present invention is directed to novel peptides which are carriers for pharmaceutical compositions.

More specifically, the invention is directed to novel IFN-receptor binding peptides that are designed as carriers for pharmaceutical compositions.

To this end, in one of its aspects, this invention provides a novel peptide having an amino acid sequence of CYS-LEU-LYS-ASP-ARG-HIS-ASP. (SEQ. ID NO. 1)

In another of its aspects, the invention provides a novel peptide having an amino acid sequence of ASP-GLU-SER-LEU-LEU-GLU-LYS-PHE-TYR-THR-GLU-LEU-TYR-GLN-GLN-LEU-ASN-ASP. (SEQ. ID NO. 2)

In still another of its aspects, the invention provides a novel peptide having a sequence of amino acids as follows: ASN-GLU-THR-ILE-VAL-GLU-ASN-LEU-LEU-ALA-ASN-VAL-TYR-HIS-GLN-ILE-ASN-HIS. (SEQ. ID NO. 3)

In another of its aspects, the invention provides a novel peptide having an amino acid sequence of: TYR-LEU-THR-GLU-LYS-LYS-TYR-SER-PRO-CYS-ALA. (SEQ. ID NO. 4)

The invention also provides a novel peptide having an amino acid sequence of: TYR-PHE-GLN-ARG-ILE-THR-LEU-TYR-LEU-THR-GLU-LYS-LYS-TYR-SER-PRO-CYS-ALA. (SEQ. ID NO. 5)

A further aspect of the invention is the provision of a novel peptide having an amino acid sequence of: TYR-PHE-GLN-ARG-ILE-THR-LEU-TYR. (SEQ. ID NO. 6)

A still further aspect of the invention is the provision of a novel peptide having an amino acid sequence of: GLU-LEU-TYR-GLN-GLN-LEU-ASN-ASP. (SEQ. ID NO. 7)

In yet another of its aspects, the invention provides a pharmaceutical composition which comprises an active drug and a suitable carrier, the carrier having been selected from the group of peptides having an amino acid sequence of CYS-LEU-LYS-ASP-ARG-HIS-ASP (SEQ. ID NO. 1); ASP-GLU-SER-LEU-LEU-GLU-LYS-PHE-TYR-THR-GLU-LEU-TYR-GLN-GLN-LEU-ASN-ASP (SEQ. ID NO. 2); ASN-GLU-THR-ILE-VAL-GLU-ASN-LEU-LEU-ALA-ASN-VAL-TYR-HIS-GLN-ILE-ASN-HIS (SEQ. ID NO. 3); TYR-LEU-THR-GLU-LYS-LYS-TYR-SER-PRO-CYS-ALA (SEQ. ID NO. 4); TYR-PHE-GLN-ARG-ILE-THR-LEU-TYR-LEU-THR-GLU-LYS-LYS-TYR-SER-PRO-CYS-ALA (SEQ. ID NO. 5); TYR-PHE-GLN-ARG-ILE-THR-LEU-TYR (SEQ. ID NO. 6); and GLU-LEU-TYR-GLN-GLN-LEU-ASN-ASP (SEQ. ID NO. 7).

The invention also provides a pharmaceutical composition which comprises an active drug and a suitable carrier, the carrier having been selected from the group of peptides substantially of the formula: CYS-LEU-LYS-ASP-ARG-HIS-ASP (SEQ. ID NO. 1); ASP-GLU-SER-LEU-LEU-GLU-LYS-PHE-TYR-THR-GLU-LEU-TYR-GLN-GLN-LEU-ASN-ASP (SEQ. ID NO. 2); ASN-GLU-THR-ILE-VAL-GLU-ASN-LEU-TYR-ALA-ASN-VAL-VAL-HIS-GLN-ILE-ASN-HIS (SEQ. ID NO. 3); TYR-LEU-THR-GLU-LYS-LYS-TYR-SER-PRO-CYS-ALA (SEQ. ID NO. 4); TYR-PHE-GLN-ARG-ILE-THR-LEU-TYR-LEU-THR-GLU-LYS-LYS-TYR-SER-PRO-CYS-ALA (SEQ. ID NO. 5); TYR-PHE-GLN-ARG-ILE-THR-LEU-TYR (SEQ. ID NO. 6); and GLU-LEU-TYR-GLN-GLN-LEU-ASN-ASP (SEQ. ID NO. 7).

FIGURE LEGENDS

FIG. 1

Figure 1:
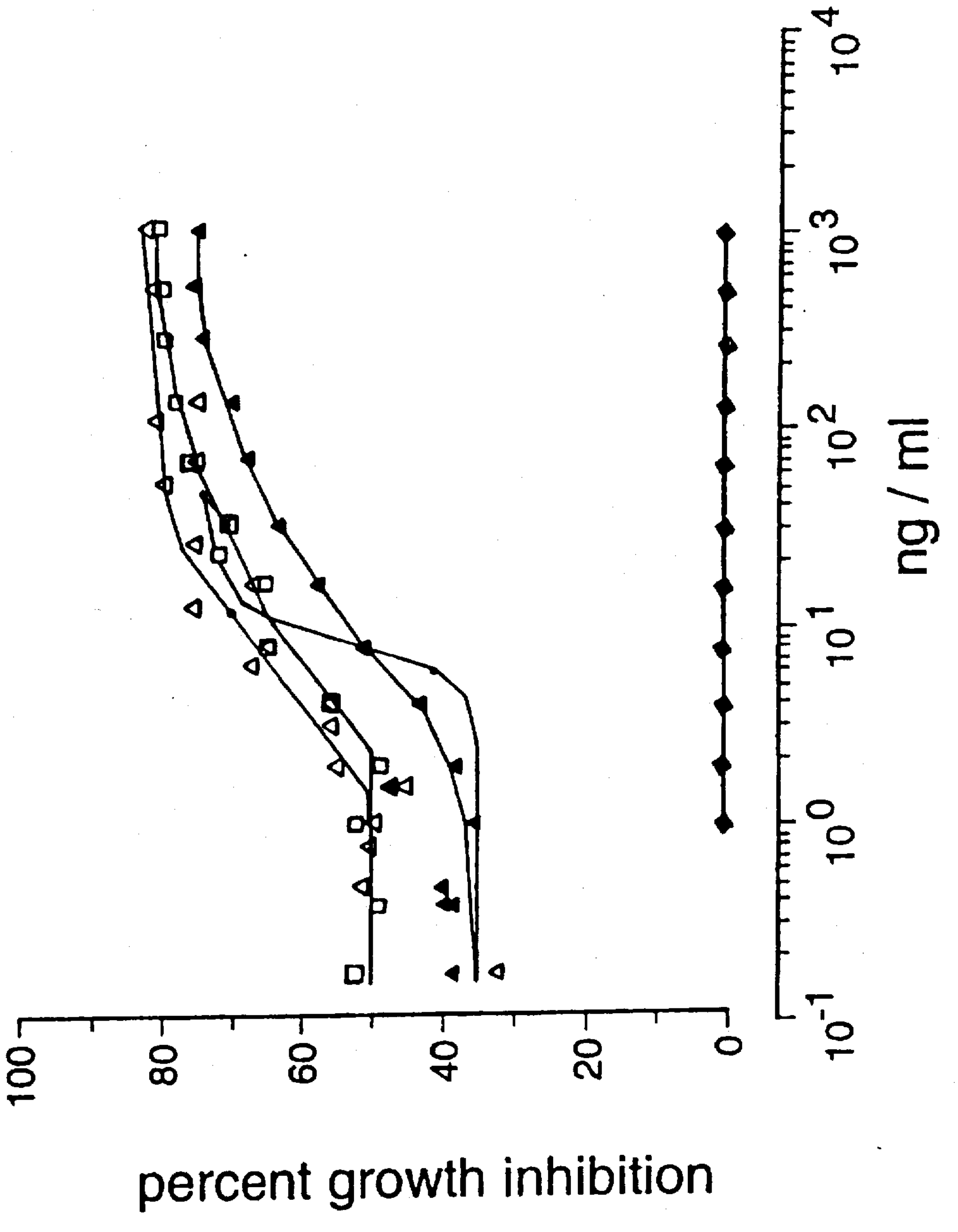
FIG. 1 illustrates the growth inhibitory activities of variant IFN-alphas in T98G cells.
Figure 2A:
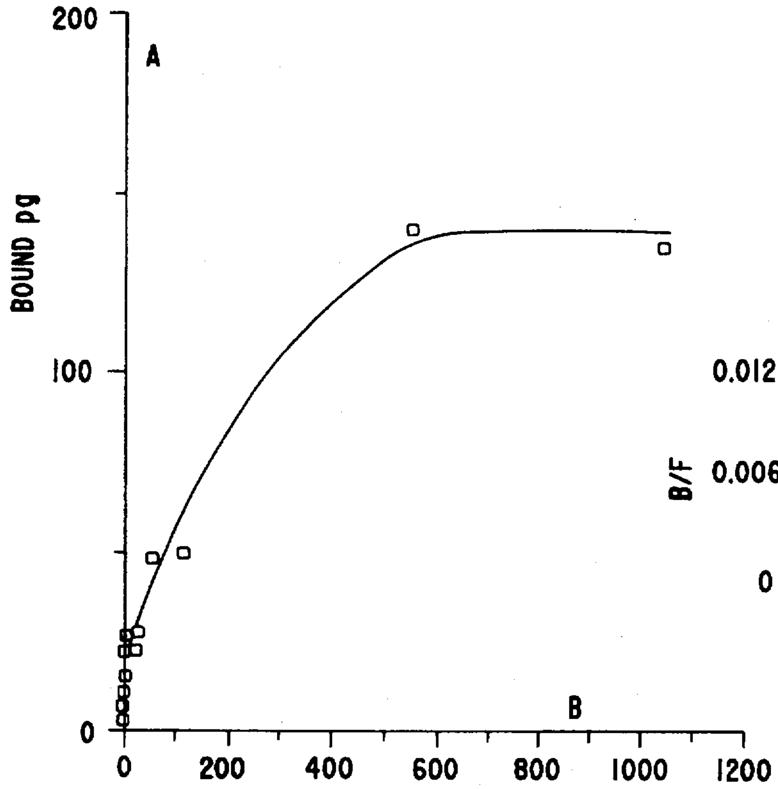
FIG. 2 shows five charts illustrating receptor binding characteristics of variant IFN-alphas on T98G cells.
Figure 2A:
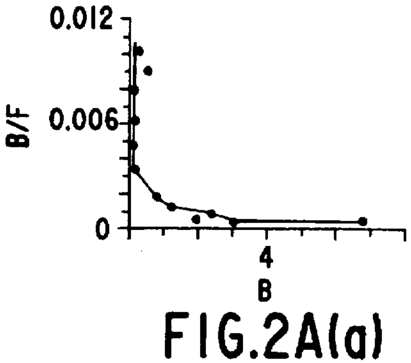
Figure 2B:
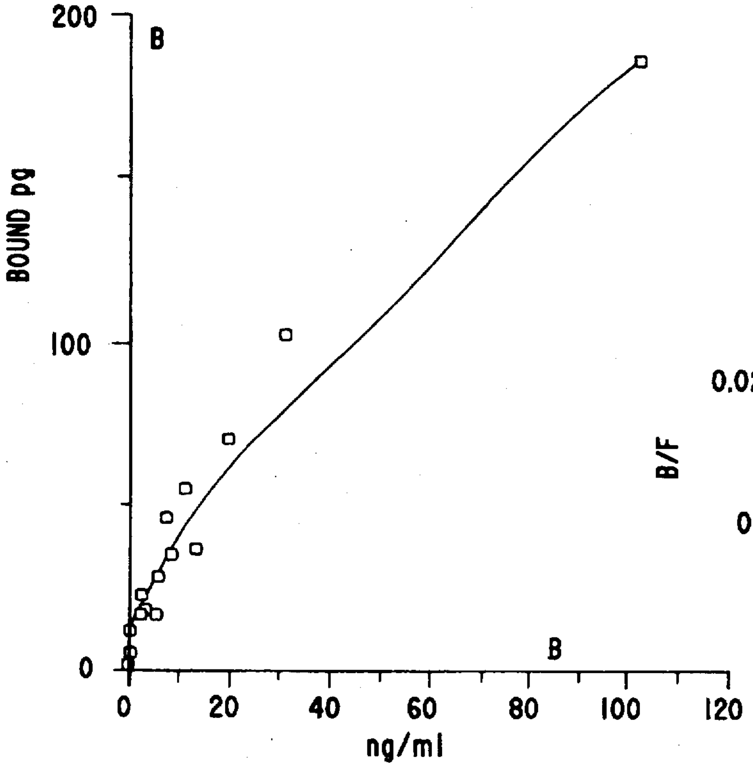
Figure 2B:
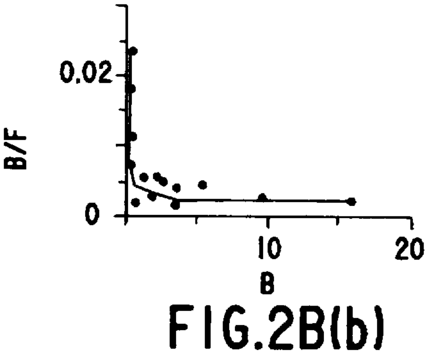
Figure 2C:
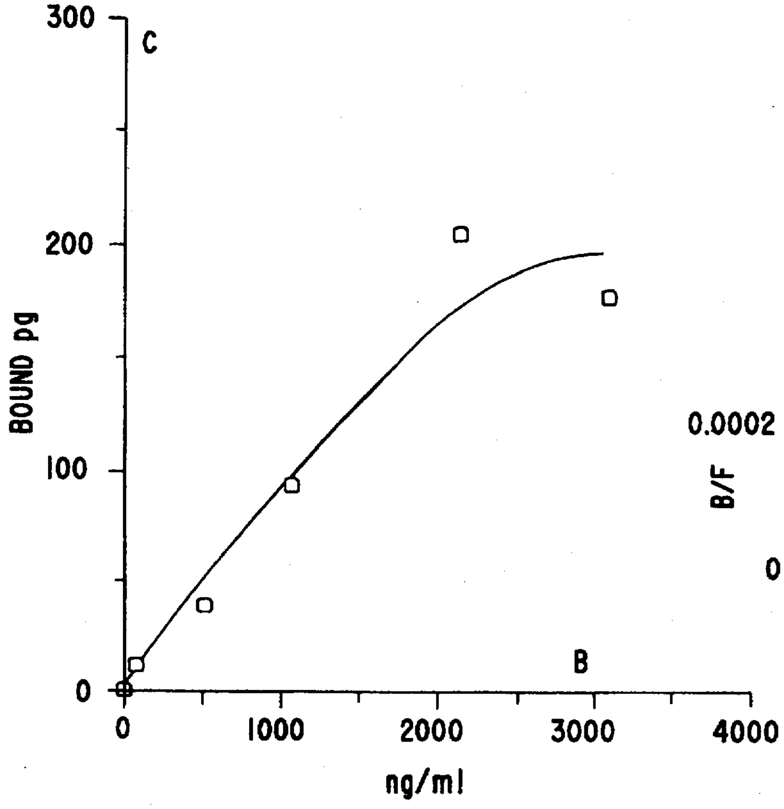
Figure 2C:
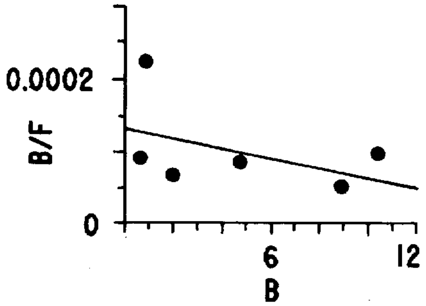
Figure 2D:
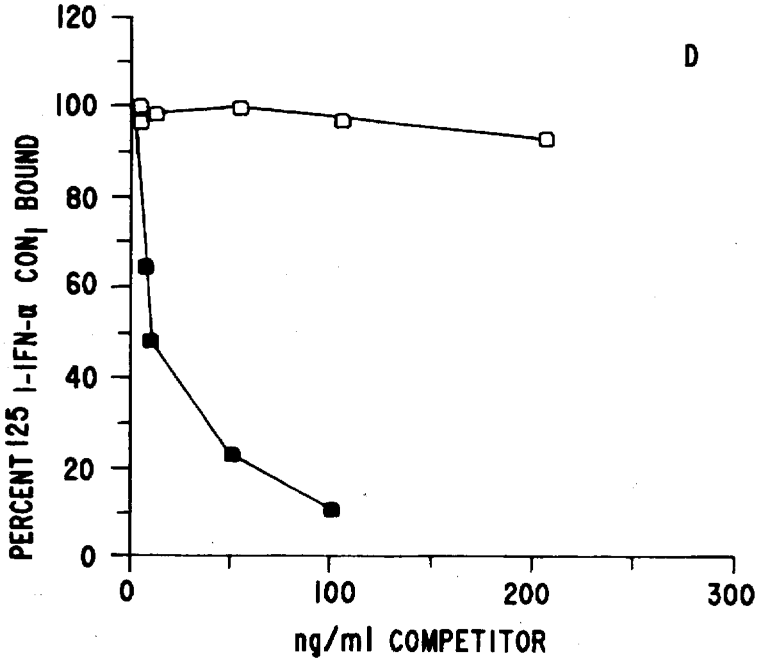
Figure 3A:
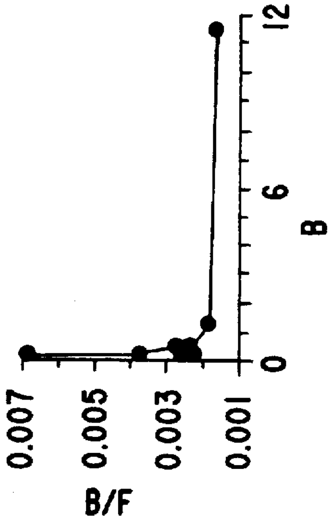
FIG. 3 shows four charts illustrating receptor binding characteristics of variant IFN-alphas on T98G cells.
Figure 3A:
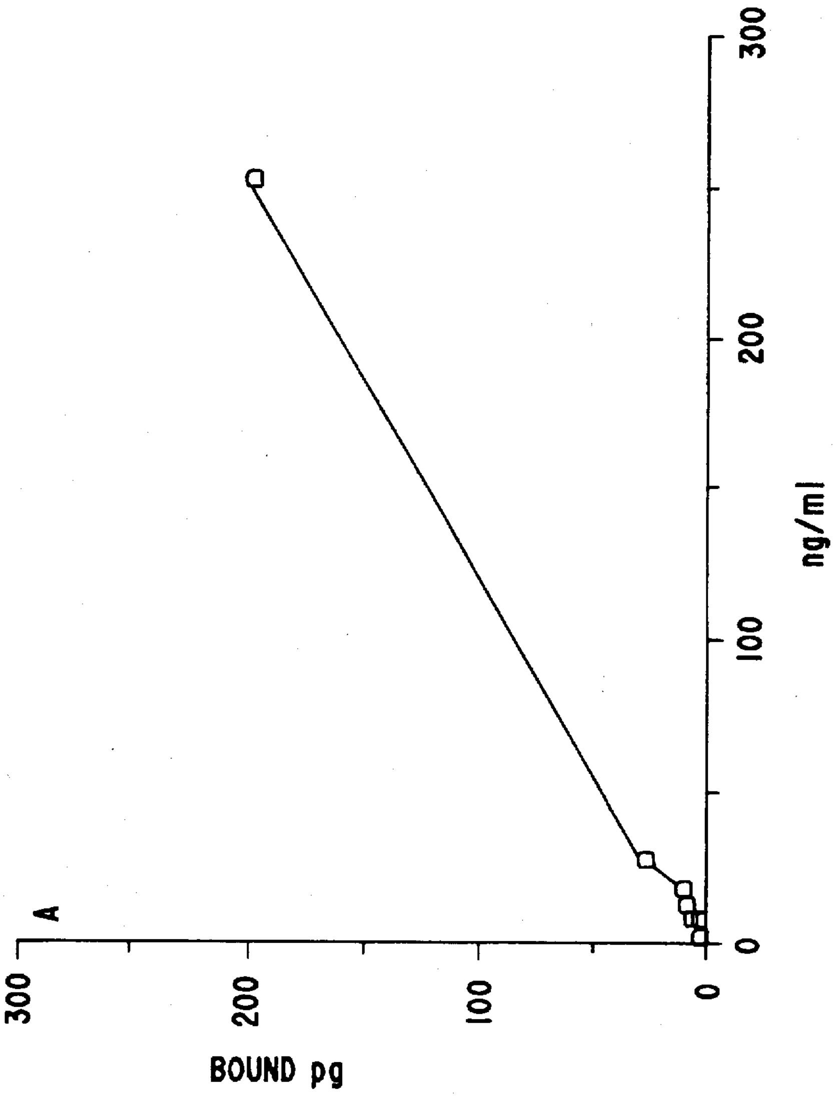
Figure 3B:
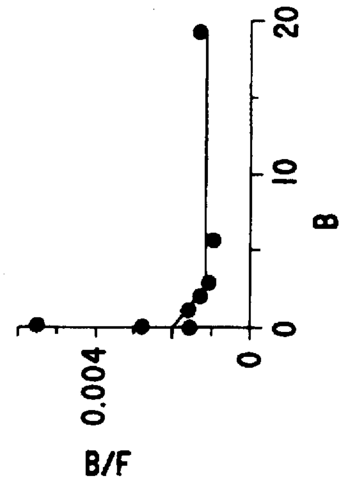
Figure 3B:
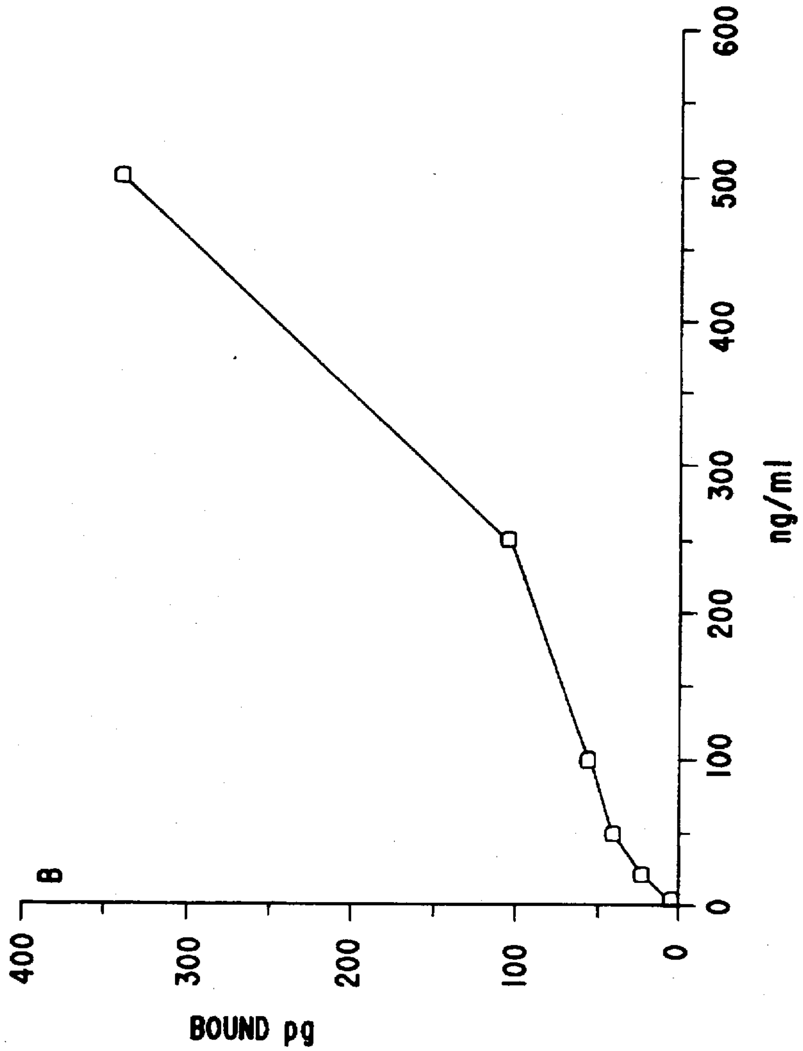
Figure 4A:
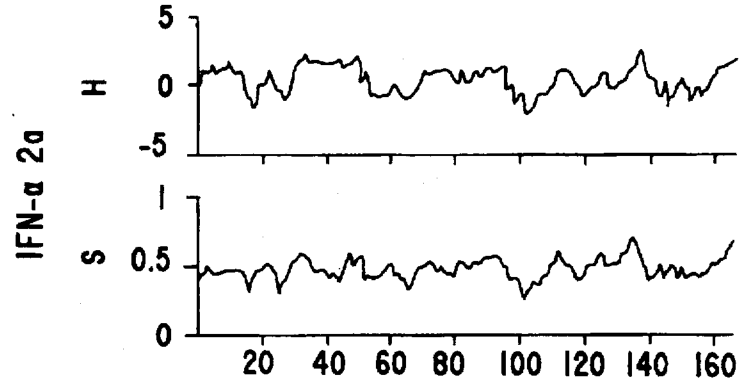
FIG. 4 shows secondary structure characteristics of different IFN-alpha species according to amino acid sequence analyses.
Figure 4A:
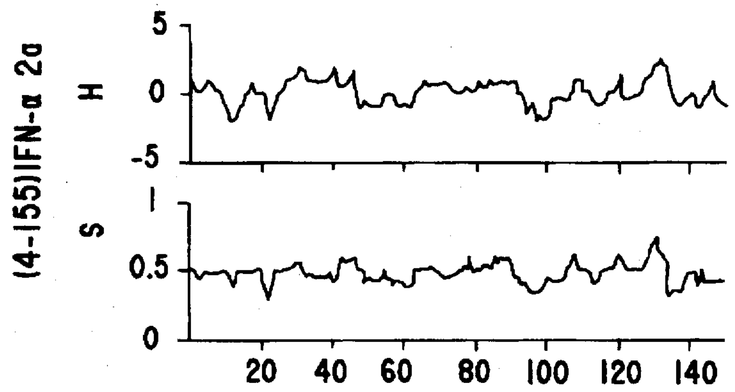
Figure 4A:
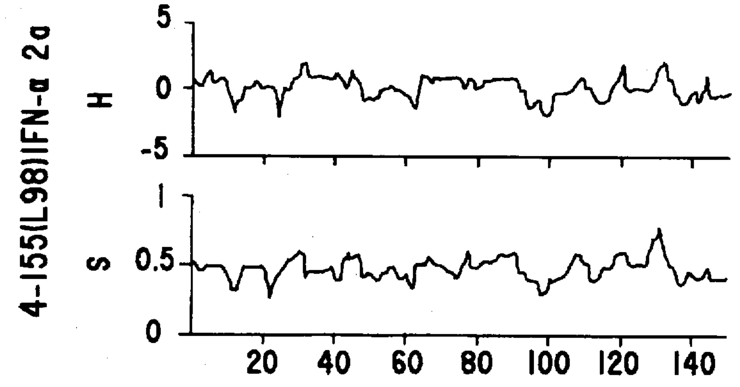
Figure 4A:
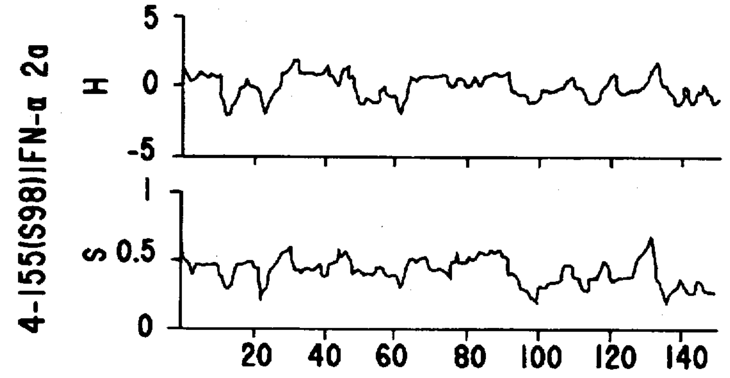
Figure 4B:
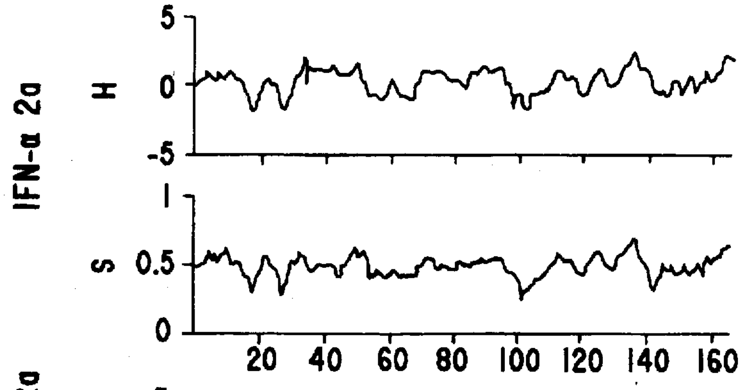
Figure 4B:
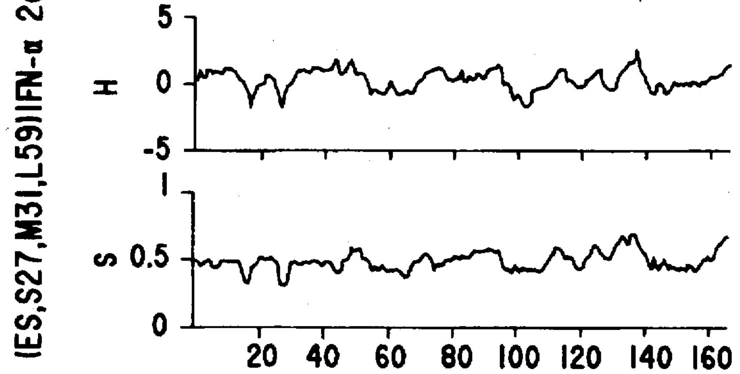
Figure 4B:
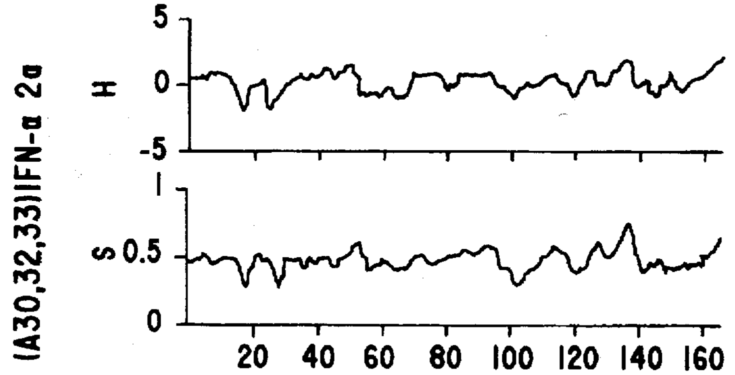
Figure 4B:
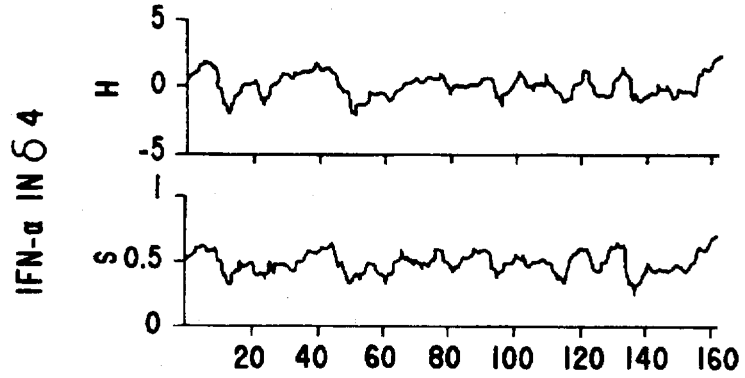
Figure 4C:
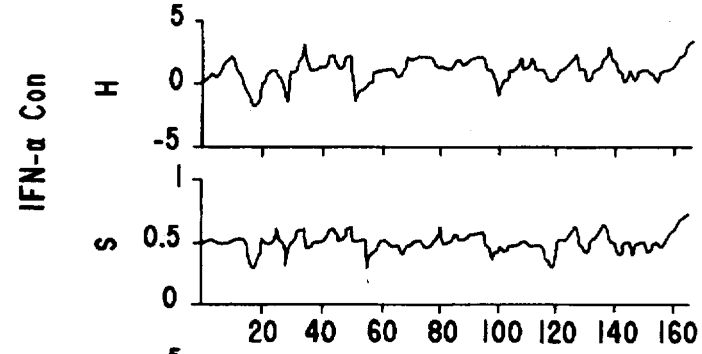
Figure 4C:
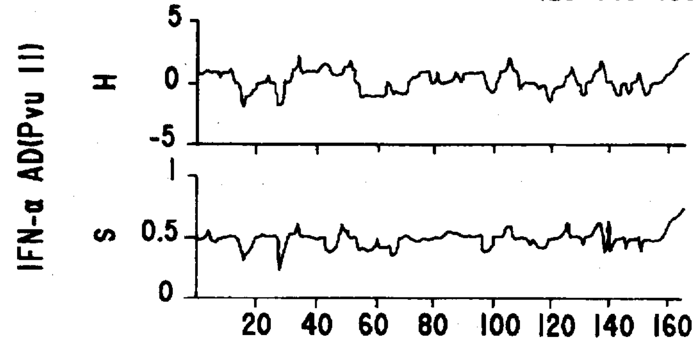
Figure 4C:
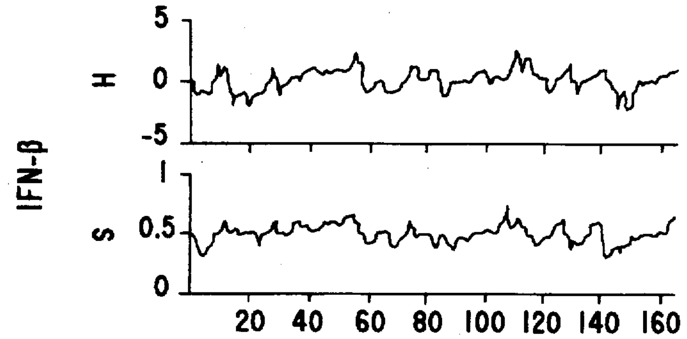
Figure 4C:
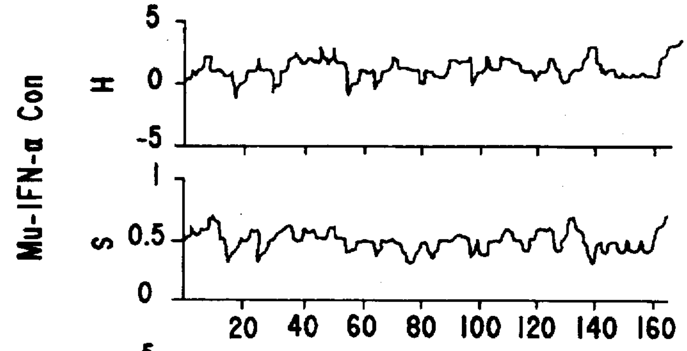
Figure 4C:
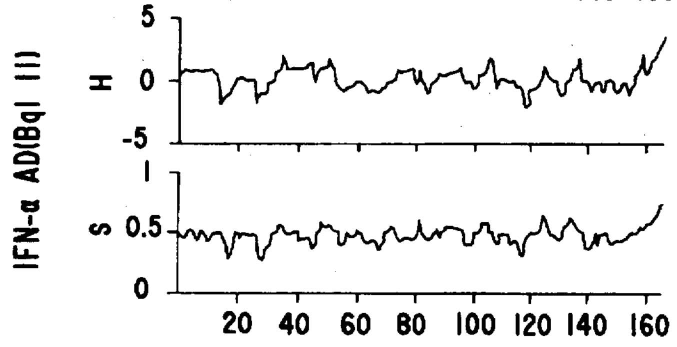

Growth inhibitory activities of variant IFN-αs in T98G cells.

Cells were incubated with the different IFN-α species, at the indicated doses, at 37° C. for 96 hr, then growth inhibition was estimated by spectrophotometric determination, as described.

Values represent the average of triplicate determinations and exhibited a SE of ±4%. □ IFN-α2a; ■ (4-155)IFN-α2a; Δ 4-155(S98)IFN-α2a; ▲ 4-155(L98)IFN-α2a; ◇ (ESML) IFN-α2a; ♦ (A30,32,33)IFN-α2a

FIG. 2

Receptor binding characteristics of variant IFN-αs on T98G cells.

Binding isotherms. $3.5\times10^5$ T98G cells were incubated for 2 hr at +4° C. with the indicated concentrations of $^{125}$I-IFN-αCon$_1$, (A), $^{125}$I-4-155(S98)IFN-α2a, (B), or $^{125}$I-IFN-α1Nδ4, (C). Inset into A, B and C are the corresponding Scatchard plots.

Competitive displacement profiles. $3.5\times10^5$ T98G cells were incubated at +4° C. for 2 hr with 10 ng/ml $^{125}$I-IFN-αCon$_1$, (D), 3.7 ng/ml $^{125}$I-4-155(S98)IFN-α2a, (E), or 300 ng/ml $^{125}$I-IFN-α1Nδ4, (F), containing no unlabeled competitor (100% bound) or the indicated concentrations of IFNs.

For D and F: ■ IFN-αCon$_1$; □ IFN-α1Nδ4.

For E: ■ IFN-α2a; □ 4-155(S98)IFN-α2a; Δ 4-155(L98) IFN-α2a.

The values shown were obtained by subtracting non-specific counts/min bound from total counts/min bound. Non-specific binding was determined in the presence of a 100-fold excess of unlabeled IFN. The points represent the mean of triplicate cultures and exhibited a S.E. or ±3%.

FIG. 3

Receptor binding characteristics of variant IFN-αs on T98G cells.

Binding isotherms $3.5\times10^5$ T98G cells were incubated for 2 hr at +4° C. with the indicated concentrations of $^{125}$I-(4-155)IFN-α2a, (A), and $^{125}$I-4-155(L98)IFN-α2a, (B). Inset into A and B are the corresponding Scatchard plots.

Competitive displacement profiles $3.5\times10^5$ T98G cells were incubated at +4° C. for 2 hr with 20 ng/ml $^{125}$I-(4-155)IFN-α2a, (C), or 8 ng/ml $^{125}$I-4-155 (L98)IFN-α2a, (D), containing no unlabeled competitor (100% bound) or the indicated concentrations of IFNs.

■ IFN-α2a; □ (4-155)IFN-α2a; Δ 4-155(L98)IFN-α2a; ▲ (ESML)IFN-α2a; ◇ (A30,32,33)IFN-α2a.

The values shown were obtained by subtracting non-specific counts/min bound from total counts/min bound. Non-specific binding was determined in the presence of a 100-fold excess of unlabeled IFN. The points represented the mean of triplicate cultures and exhibited a S.E. of ±3%

FIG. 4

Predicted secondary structure characteristics of different IFN-α species according to amino acid sequence analyses. Hydrophilicity, H, and surface probability, S, profiles are depicted for each of the IFN-αs and IFN-β, whose designations are on the left hand side of each pair. Amino acid residue position is indicated along the horizontal axes of the graphs. The critical domains, comprising residues 29–35, 78–95 and 123–140, are boxed.

FIG. 5

Model for the tertiary structure of Type I IFNs.

This model incorporates a helical bundle core, composed of the 5 helices A-E. The loop structures that constitute the proposed receptor recognition epitopes, residues 29–35 and 130–140, shown here as heavily shaded, broad lines, are aligned such that they dock in the receptor groove as shown. The third region implicated in the active conformation of the Type I IFNs, 78–95, is not buried in the receptor groove and is configured to allow binding to its cognate epitope on another Type 1 IFN receptor. The shaded areas in helices C and D represent residues that are critical for maintaining the correct structural presentation of the corresponding contiguous recognition epitopes (see text).

DESCRIPTION OF THE PREFERRED EMBODIMENT

Biologically active proteins have an optimum active configuration that is composed of discrete and unique strategic domains along the polypeptide. These critical structural domains determine such parameters as receptor binding and effector functions. Characterization of these strategic domains, that includes defining their spatial configuration and effector functions, will clarify the sequence of events comprising and initiated by receptor binding and that lead to specific biological responses.

For a therapeutic agent to be optimally active, it must be delivered to the specific site of action intact and must interact with the target tissues. In a number of clinical conditions, such as uncontrolled proliferation in neoplastic tissues, or infected tissues, or inflamed tissues, the cells express abundant Type 1 IFN receptors, that is, IFN-alpha and IFN-beta receptor expression at the cell surface is upregulated. It has been determined that specific peptides are capable of recognizing and binding to these cell surface receptors. Once bound, the ligand-IFN receptor complex is transported into the cell.

The present invention relates therefore to novel carriers which comprise peptides of specific amino acid sequences. These sequences are:

(i) an amino acid sequence of CYS-LEU-LYS-ASP-ARG-HIS-ASP (SEQ. ID NO. 1);

(ii) an amino acid sequence of ASP-GLU-SER-LEU-LEU-GLU-LYS-PHE-TYR-THR-GLU-LEU-TYR-GLN-GLN-LEU-ASN-ASP (SEQ. ID NO. 2);

(iii) an amino acid sequence of ASN-GLU-THR-ILE-VAL-GLU-ASN-LEU-LEU-ALA-ASN-VAL-TYR-HIS-GLN-ILE-ASN-HIS (SEQ. ID. NO. 3);

(iv) an amino acid sequence of:TYR-LEU-THR-GLU-LYS-LYS-TYR-SER-PRO-CYS-ALA (SEQ. ID NO. 4);

(v) an amino acid sequence of: TYR-PHE-GLN-ARG-ILE-THR-LEU-TYR-LEU-THR-GLU-LYS-LYS-TYR-SER-PRO-CYS-ALA (SEQ. ID NO. 5);

(vi) an amino acid sequence of: TYR-PHE-GLN-ARG-ILE-THR-LEU-TYR (SEQ. ID NO. 6); and (vii) an amino acid sequence of: GLU-LEU-TYR-GLN-GLN-LEU-ASN-ASP (SEQ. ID NO. 7).

These novel peptide/carriers have been incorporated into interferons to establish their claimed utility. The following description will be made in conjunction with experiments using interferons having the novel carriers incorporated therein but the invention is not to be restricted to such interferons.

Fish et al in *J. IFN Res.* (1989) 9, 97–114 have identified three regions in IFN-alpha that contribute toward the active configuration of the molecule. These three regions include: 10–35, 78–107 and 122–166.

The structural homology and symmetry observed among a number of haemopoietic cytokine receptors, and specifically the IFN receptors and tissue factor, the membrane receptor for the coagulation protease factor VII, lends support to the functional receptor binding model that was proposed by Bazan, J. F., *Pro. Natl. Acad. Sci.* (1990) 87, 6934–6938. This model invokes the presence of a generic binding through that allows recognition of conserved structural elements among different cytokines. The present inventor's data supports such a model, at least for the different IFN-alpha molecular species and IFN-beta, since they have identified two conserved elements in the Type 1 IFNs that effect receptor recognition. A third structural element, that is an exposed recognition epitope, confers specificity of cytokine function, including species specificity.

Experiments were conducted using IFNs shown in Table 1:

TABLE 1

| | 1 | 11 | 21 | 31 | | |
|---|---|---|---|---|---|---|
| IFN-$\alpha$Con$_1$ | CDLPQTHSLG | NRRTLILLAQ | MRRISPFS | CL | KDRHD | FGFPQ |
| IFN-$\alpha$2a | CDLPQTHSLG | SRRTLMLLAQ | MRRISLFS | CL | KDRHD | FGFPQ |
| (4-155)IFN-$\alpha$2a | QTHSLG | SRRTLMLLAQ | MRRISLFS | CL | KDRHD | FGFPQ |
| 4-155(S98)IFN-$\alpha$2a | QTHSLG | SRRTLMLLAQ | MRRISLFS | CL | KDRHD | FGFPQ |
| 4-155(L98)IFN-$\alpha$2a | QTHSLG | SRRTLMLLAQ | MRRISLFS | CL | KDRHD | FGFPQ |
| (ESML)IFN-$\alpha$2a | CDLPETHSLG | SRRTLMLLAQ | MRRISLSS | CL | MDRHD | FGFPQ |
| (A30,32,33)IFN-$\alpha$2a | CDLPQTHSLG | SRRTLMLLAQ | MRRISLFS | CA | KAAHD | FGFPQ |
| IFN-$\alpha$1N$\delta$4 | ETHSLD | NRRTLMLLAQ | MSRISPSS | CL | MDRHD | FGFPQ |
| IFN-$\beta$ | MSYNLLGFLQRSS | NFQCCKLLWQ | LNGRLEYCL | | KDRMN | FDIPE |
| MuIFN-$\alpha$Con | CDLPQTHNLR | NKRAITLLVQ | MRRLSPLS | CL | KDRKD | FGFPQ |

| | 41 | 51 | 61 | 71 |
|---|---|---|---|---|
| IFN-$\alpha$Con$_1$ | EEFDGNQFQK | AQAISYLHEM | IQQTFNLFST | KDSSAAWDES |
| IFN-$\alpha$2a | EEF-GNQFQK | AETIPVLHEM | IQQIFNLFST | KDSSAAWDET |
| (4-155)IFN-$\alpha$2a | EEF-GNQFQK | AETIPVLHEM | IQQIFNLFST | KDSSAAWDET |
| 4-155(S98)IFN-$\alpha$2a | EEF-GNQFQK | AETIPVLHEM | IQQIFNLFST | KDSSAAWDET |
| 4-155(L98)IFN-$\alpha$2a | EEF-GNQFQK | AETIPVLHEM | IQQIFNLFST | KDSSAAWDET |
| (ESML)IFN-$\alpha$2a | EFF-GNQFQK | AETIPVLHLM | IQQIFNLFST | KDSSAAWDET |
| (A30,32,33)IFN-$\alpha$2a | EEF-GNQFQK | AETIPVLHLM | IQQIFNLFST | KDSSAAWDET |
| IFN-$\alpha$1N$\delta$4 | EEFDGNQFQK | APAISVHLEL | IQQIFNLFTT | KDSSAAWDED |
| IFN-$\beta$ | EEIKQLQQFQK | EDAALTUYEM | LQNIFAIFRQ | DSSSTGWNET |
| MuIFN-$\alpha$Con | EKVDAQQIQK | AQAIPVLSEL | TQQILNIFTS | KDSSAAWNAT |

| | 81 | 91 | | 101 | 111 |
|---|---|---|---|---|---|
| IFN-$\alpha$Con$_1$ | LLEKFYTELY | QQLND | LEACY | IQEVGVEETP | LMNVDSILAV |
| IFN-$\alpha$2a | LLDKFYTELY | QQLND | LEACY | IQGVGVTETP | LMKEDSLAV |
| (4-155)IFN-$\alpha$2a | LLDKFYTELY | QQLND | LEACY | IQGVGVTETP | LMKEDSLAV |
| 4-155(S98)IFN-$\alpha$2a | LLDKFYTELY | QQLND | LEACY | IQGVGVTETP | LLKEDSLAV |
| 4-155(L98)IFN-$\alpha$2a | LLDKFYTELY | QQLND | LEACY | IQGVGVTETP | LMKEDSLAV |
| (ESML)IFN-$\alpha$2a | LLDKFYTELY | QQLND | EEACY | IQGGVVTETP | LMKEDSLAV |
| (A30,32,33)IFN-$\alpha$2a | LLDKFYTELY | QQLND | LEACY | IQGVGVTETP | LMKEDSLAV |
| IFN-$\alpha$1N$\delta$4 | LLDKFCTELY | QQLND | LEACY | MQEERVGETP | LMNADSILAV |
| IFN-$\beta$ | IVENLLANW | HQINH | LKTVL | EEKLEKEDFT | RGKLMSSLHL |
| MuIFN-$\alpha$Con | LLDSFCNDLH | QQLND | LQACL | MQEVGVQEPP | LTQEDSLLAV |

| | 121 | | 131 | 141 | 151 |
|---|---|---|---|---|---|
| IFN-$\alpha$Con$_1$ | RK | YFQRITLY | LTEKKYSPCA | WEVVRAEIMR | SFSLSTNLQE |
| IFN-$\alpha$2a | RK | YFQRITLY | LTEKKYSPCA | WEVVRAEIMR | SFSLSTNLQE |
| (4-155)IFN-$\alpha$2a | RK | YFQRITLY | LTEKKYSPCA | WEVVRAEIMR | SFSLS |
| 4-155(S98)IFN-$\alpha$2a | RK | YFQRITLY | LTEKKYSPCA | WEVVRAEIMR | SFSLS |
| 4-155(L98)IFN-$\alpha$2a | RK | YFQRITLY | LTEKKYSPCA | WEVVRAEIMR | SFSLS |
| (ESML)IFN-$\alpha$2a | RK | YFQRITLY | LTEKKYSPCA | WEVVRAEIMR | SFSLSTNLQE |
| (A30,32,33)IFN-$\alpha$2a | RK | YFQRITLY | LTEKKYSPCA | WEVVRAEIMR | SFSLSTNLQE |
| IFN-$\alpha$1N$\delta$4 | KK | YFRRITLY | LTEKKYSPCA | WEVVRAEIMR | SFSLSTNLQE |
| IFN-$\beta$ | KR | YYGRILHY | LKAKEYSHCA | WTIVAVEILR | NFYLINRLTG |
| MuIFN-$\alpha$Con | RK | YFHRITVV | LREKKHSPCA | WEVVRAEVWR | ALSSSANLLA |

TABLE 1-continued

| | 161 |
|---|---|
| IFN-αCon$_1$ | RLRRKE |
| IFN-α2a | SLRSKE |
| (4-155)IFN-α2a | |
| 4-155(S98)IFN-α2a | |
| 4-155(L98)IFN-α2a | |
| (ESML)IFN-α2a | SLRSKE |
| (A30,32,33)IFN-α2a | SLRSKE |
| IFN-α1Nδ4 | RLRRKE |
| IFN-β | YLRN |
| MuIFN-αCon | RLSEEKE |

Table 1

The foregoing table illustrates the amino acid sequence alignment of the different Type 1 IFNs. The designation of the various IFNs is shown in the left hand column and the sequence of IFN-beta is aligned with the other IFNs, commencing with residue 4, to achieve the greatest homology. The critical domains comprising residues 29–35, 78–95 and 123–140 are boxed. The letter codes for the amino acids are as follows: A, ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

IFN-alpha2a and the various derivatives were provided by I.C.I. Pharmaceuticals Division of the UK; IFN-alphaCon$_1$ was supplied by Amgen of the USA and IFN-alpha$_1$Nδ4 was supplied by Schering Plough Corp of the USA.

IFN-alpha2a, (4-155)IFN-alpha2a, 4-155(S98)IFN-alpha2a and 4-155(L98)IFN-alpha2a had specific activities of $2\times10^8$ U/mg protein; (A30,32,33)IFN-alpha2a was inactive in antiviral assays and (ESML)IFN-alpha2a had a specific activity of $7.5\times10^6$U/mg protein; IFN-alphaCon$_1$ had a specific activity of $3.0\times10^9$U/mg protein; and IFN-alpha$_1$Nδ4 had a specific activity of $7.1\times10^6$U/mg protein.

The cell culture used comprised T98G cells which were derived from a human glioblastoma multiforma tumor and which express in culture a number of normal and transformed growth characteristics. These cells may be routinely subcultured as monolayers, in modified minimum essential medium (hereinafter referred to as alpha-MEM), and supplemented with 10% (v/v) fetal calf serum (hereinafter referred to as FCS).

An in vitro assay for antiviral activity was conducted. T98G cells were seeded at a density of $1.5\times10^5$/ml in 200 µl alpha-MEM supplemented with 10% FCS in 96-well Microtest (trade mark) II tissues culture plates and treated with dilutions of the IFN preparations for 24 hours. At the time of virus innoculation, the IFNs were removed and $10^4$ PFU EMCV was added to individual wells in 100 µl alpha-MEM, 2% FCS. After 24 hours, the cells were ethanol (95%) fixed and the extent of EMCV infection was determined by spectrophotometric estimation of viral CPE. The fixed cells were crystal violet (0.1% in 2% ethanol) stained and destained (0.5M NaCl in 50% ethanol), and the inhibition of virus infection was estimated from absorbance measurements at 570 nm using a Microplate (trade mark) Reader MR600 and a calibration of absorbance against cell numbers. IFN titers were determined using a 50% cytopathic end-point and converted to international units using an NIH IFN-alpha standard (Ga 23-901-527).

An in vitro assay for growth inhibitory activity was conducted. T98G cells were seeded in 96-well Microtest II tissue culture plates at a density of $5\times10^3$/ml and either innoculated with two-fold serial dilutions of different molecular species of IFN-alpha or left untreated. After incubation, at 37° C. for 96 hours, the cells were ethanol fixed (95%), crystal violet (0.1% in 2% ethanol) stained and destained (0.5M NaCl in 50% ethanol), then growth inhibition was estimated from absorbance measurements of destained cells at 570 nm (using a Microplate Reader MR600 and a-calibration of absorbance against cell numbers).

The results of these experiments are shown in FIG. 1. The values represented are the average of triplicate determinations and exhibited a SE of +/−4%. Whereas IFN-alpha2a, (4-155)IFN-alpha2a, 4-155(S98)IFN-alpha2a and 4-155(L98)IFN-alpha2a demonstrate comparable growth inhibitory activities within the error of the assay, (ESML)IFN-alpha2a and (A30,32,33)IFN-alpha2a do not exhibit antiproliferative activity. Similarly, IFN-alpha$_1$Nδ4 has minimal antiviral activity ($7.1\times10^6$ U/mg protein) and no demonstrable antiproliferative activity over the dose range examined.

The next series of experiments examined IFN-receptor interactions. Labelling was carrier out using $^{125}$I using a solid phase lactoperoxidase method. A 100 µl reaction mixture containing 10 µl 3% B-D-glucose, 10 µl hydrated Enzymo-beads (trade mark) (available from BioRad in California, USA) 2 µCi Na$^{125}$I and 20 µg HuIFN-alpha in PBS, pH 7.2, was reacted overnight at +4° C. Free $^{125}$I was separated from IFN-bound $^{125}$I on a 12 ml Sephadex (trade mark) G-75 column, equilibrated in PBS containing 1 mg/ml BSA. Iodination caused no detectable loss of antiviral activity. Fractions containing maximum antiviral activity were pooled and contained 95% TCA (10%) precipitable radioactivity.

Sub-confluent cell monolayers were incubated at +4° C. in alpha-MEM containing 2% FCS and indicated concentrations of $^{125}$I-IFN-alpha. After 2 hours, the binding medium was aspirated and the cultures were washed twice with ice-cold PBS. The cells were solubilized in 0.5M NaOH and radioactivity counted in a Beckman (trade mark) 5500 *-counter. Specificity of binding was determined in parallel binding assays containing a 100-fold excess of unlabeled growth factor. For competitive experiments, specified amounts of unlabeled competitor were included in the reaction mixture together with radiolabelled ligand.

Specific $^{125}$I-IFN-alpha binding data were used to determine receptor numbers and dissociation constants, $K_d$. With increasing concentrations of $^{125}$I-ligand in the cellular binding reactions, respective specific binding activities corresponding to each $^{125}$I-ligand concentration was calculated.

In FIG. 2, panel A illustrates the results using $^{125}$I-IFN-alphaCon$_1$; panel B illustrates the results using $^{125}$I-4-155(S98)IFN-alpha2a; and panel C illustrates the results using $^{125}$I-IFN-alpha$_1$Nδ4. Inset into panels A, B and C are the corresponding Scatchard plots. The competitive displacement profiles are shown in panels D, E and F using 10 ng/ml of $^{125}$I-IFN-alphaCon$_1$, 3.7 ng/ml of $^{125}$I-4-155(S98)IFN-alpha2a and 300 ng/ml of $^{125}$I-IFN-alpha$_1$Nδ4 respectively, with no unlabeled competitor (100% bound) or the indicated concentrations of IFNs. The values shown were obtained by subtracting non-specific counts/min bound from total counts/min bound. Non-specific binding was determined in the presence of a 100-fold excess of unlabeled IFN. The points represent the mean of triplicate cultures and exhibited a S.E. of +/−3%.

In FIG. 3, panel A illustrates the results using $^{125}$I-(4-155)IFN-alpha2a and panel B illustrates the results using $^{125}$I-4-155(L98)IFN-alpha2a. Inset into panels A and B are the corresponding Scatchard plots. The competitive displacement profiles are shown in panels C and D using 20 ng/ml of $^{125}$I-(4-155)IFN-alpha2a and 8 ng/ml of $^{125}$I-4-155 (L98)IFN-alpha2a, with no unlabeled competitor (100% bound) or the indicated concentrations of IFNs. The values shown were obtained by subtracting non-specific counts/min bound from total counts/min bound. Non-specific binding was determined in the presence of a 100-fold excess of unlabeled IFN. The points represent the mean of triplicate cultures and exhibited a S.E. of +/−3%.

FIGS. 2 and 3 illustrate the steady state receptor binding characteristics of the different IFN-alpha molecular species on T98G cells at +4° C. Specific binding to sub-confluent T98G monolayers is resolved into a biphasic Scatchard plot. This IFN binding heterogeneity has been shown to result from negatively cooperative site-site interactions between the ligand receptors. Analysis of the IFN-alpha2a binding data reveals both high and low affinity binding components, with $K_d$s of 2–3×10$^{-11}$M and 2–5×10$^{-9}$M, respectively. It was found that $^{125}$I(ESML) IFN-alpha2a exhibited no detectable binding activity on proliferating (log phase) T98G cells at +4° C. $^{125}$I-IFN-alphaCon$_1$ binding to cells was resolved into high affinity $K_d$ 7.7×10$^{-12}$M) and low affinity ($K_d$ 1.4×10$^{-9}$M) components as shown in FIG. 2A. Similarly, $^{125}$I-4-155(S98)IFN-alpha2a (FIG. 2B), $^{125}$I(4-155)IFN-alpha2a (FIG. 3A) and $^{125}$I-4-155(L98)IFN-alpha2a (FIG. 3B) exhibited binding heterogeneity on T98G cells, with high and low affinity components comparable to IFN-alpha2a. $^{125}$I-IFN-alpha$_1$Nδ4 binding to T98G cells was resolved into a monophasic Scatchard plot, with a single low affinity binding component of $K_d$ 10$^{-7}$M (FIG. 2C). Indeed, competitive binding studies with either $^{125}$I-IFN-alphaCon$_1$ (FIG. 2D) or $^{125}$I-IFN-alpha$_1$Nδ4 (FIG. 2F), confirmed that IFN-alpha$_1$Nδ4 has a weaker affinity for the IFN-alpha receptor on T98G cells than IFN-alphaCon$_1$. Substitution of the cysteine residue at position 98 in IFN-alpha2a with a serine, does not affect the polarity or charge distribution of the side chain at this position ($CH_2$—SH to $CH_2$—OH), yet substitution with a leucine residue does introduce an aliphatic side chain and hence alter the polarity ($CH_2$—SH to CH—$(CH_3)_2$). This alteration in side chain polarity at this residue position is not reflected in altered affinity characteristics for the IFN-alpha receptor (FIG. 3B). As would be anticipated, substitution of the cysteine residue at position 98 with serine, did not affect receptor binding characteristics (FIGS. 2B,E). The data from the competitive binding studies, indicate that the IFN-alpha2a variants (ESML)IFN-alpha2a and (A30,32,33)IFN-alpha2a, are unable to bind to the IFN-alpha receptor (FIGS. 3C,D).

Since the amino acid sequence dictates the native conformation of a protein, the inventor has ascribed protein structure for the different IFN-alphas and IFN-beta. Receptor recognition epitopes are characteristically hydrophilic and located on the surface of the binding molecule. Generally, sites for molecular recognition in proteins are located in loops or turns, whereas alpha-helices are involved in maintaining the structural integrity of the protein. Close examination of the hydrophilicity and surface probability plots of IFN-alpha2a shows that, in those regions that are critical for the active configuration of IFN-alpha, namely 10–35, 78–107 and 123–166, altering the cysteine at 98 has no effect on these determinants (FIG. 4), and indeed, does not affect biological activity (FIG. 1).

FIG. 4 illustrates predicted secondary structure characteristics of different IFN-alpha species according to amino acid sequence analyses. Hydrophilicity (H) and surface probability (S) profiles are depicted for each of the IFN-alphas and IFN-beta whose designations are on the left hand side of each pair. Amino acid residue position is indicated along the horizontal axes of the graphs. The critical domains comprising residues 29–35, 78–95 and 123–140 are boxed.

In IFN-alpha2a, in the carboxy-terminal domain there are essentially 3 hydrophilic residue clusters that are likely located on the surface of the molecule (FIG. 4). Deletion of the cluster closest to the carboxy-terminus, in (4-155)IFN-alpha2a, has no effect on antiviral specific activity, growth inhibitory activity (FIG. 1), or receptor binding characteristics (FIG. 3), compared with the full length IFN-alpha2a. Thus, for receptor recognition, the region 155–166 does not influence the active configuration of the previously defined strategic domain 123–166. Interestingly, there are two peaks of hydrophilicity in this carboxy-terminal region, that spans residues 123–140, that correspond to a helical bundle and loop structure. In the human, equine, bovine, ovine, rat and murine IFN-alphas, human and murine IFN-beta, cow trophoblast IFN (TP-1) and horse IFN-omega, all designated Type 1 IFNs, these structural motifs are highly conserved (FIG. 4), lending credence to the notion that this carboxy-terminally located domain is critical for receptor recognition for the Type 1 IFNs. The alpha-helical structure, that constitutes residues 123–129, allows the appropriate presentation of the loop structure around residues 130–140, and this loop structure serves as a recognition epitope for receptor binding. This conclusion is consistent with reports that the region that comprises residues 123–136 influences biological activities on human and murine cells. Further examination of the 10–35 domain, reveals a single region that is likely located on the surface of the molecule and contains hydrophilic residues, namely 29–35. Other reports have implicated the amino-terminal region of IFN-alpha, in particular amino acid residue 33, as critical for biological activity on human and bovine cells. The IFN-alpha2a variants (A30-32,33)IFN-alpha2a and (E5,S27,M31,L59)IFN-alpha2a, that have lost biological activity and receptor binding characteristics, no longer present this cluster of residues near the surface of the molecule, (FIG. 4). This region constitutes a loop structure. In IFN-alpha$_1$Nδ4, the amino acid residues that immediately precede the critical 29–35 cluster are different to those in IFN-alpha2a, and thus affect the presentation of this receptor binding epitope somewhat, according to the different predictive algorithms the inventor has employed. The data in FIG. 4 suggest that the cluster of hydrophilic residues that do constitute this receptor recognition epitope will be located near the surface of the molecule in IFN-alpha$_1$Nδ4. However, substitution of the lysine residue at position 31 by a methionine residue, affects the configuration of this receptor recognition epitope, thereby affecting the biological effectiveness of IFN-alpha$_1$Nδ4. In the human and murine IFNs, the loop structure that includes residues 29–35, is conserved, yet CLKDRHD is presented as CLKDRMN and NLTYRAD, respectively (see FIG. 3). In murine consensus IFN-alpha, MuIFN-alphaCon, this epitope is conserved as CLKDRKD, where H (histidine) to K (lysine) is a conservative change with respect to side chain group and charge. Considerable sequence homology with the human residues 29–35 is also apparent among the murine, equine, ovine, bovine and rat IFN-alphas, as well as for cow TP-1 and horse IFN-omega. The Type 1 IFNs share conserved receptor recognition epitopes in the 29–35 and 123–140 regions. Some variance is seen in the human and murine IFN-beta in the 29–35 region, although the presentation of this epitope as a loop structure is conserved.

The third strategic region with respect to the active configuration of IFN-alpha spans residues 78–107. A hydrophilic cluster of amino acid residues that are likely located on the surface constitute residues 83–95 (FIG. 4). These residues probably present as a contiguous helical bundle and a loop structure. Several amino acid residues around position 78 also appear to be located at the surface as part of the helical bundle. The inventor has shown that substitution of the cysteine at position 98 with either a serine (S) or a leucine (L) does not affect the receptor binding characteristics of IFN-alpha2a, hence the inventor infers that those residues beyond 95, in the previously defined domain 78–107, are likely not critical for receptor recognition in IFN-alpha, since they appear not to be located at the surface of the molecule. The alpha-helical structure allows the appropriate presentation of the recognition epitope that comprises residues 88–95. Of note is the variance in this region between the human IFN-alphas and the murine IFN-alphas, and the human IFN-alphas had human IFN-beta. Of the three previously defined critical active domains in the Type I IFNs, it is this domain that exhibits the most divergence with respect to species, and alpha-versus beta-IFNs (Table 1). It is noteworthy that the hybrid IFN, IFN-alphaAD(Bgl II), exhibits a hydrophilicity plot somewhat different from the human IFN-alphas in this region, yet similar to that seen for the murine IFNs, specifically MuIFN-alphaCon (FIG. 4). Both MuIFN-alphaCon and IFN-alphaAD(Bgl II) have a cysteine residue at position 86, in contrast with the majority of human IFN-alphas, for which there is a tyrosine residue in this position. These data are consistent with IFN-alphaAD(BgI II) showing demonstrable biological activity on murine cells and support the hypothesis that this region in the Type I IFNs determines species specificity. Indeed, the hybrid IFN-alphaAD(PvuII) resembles the human IFN-alphas in this region (FIG. 4) and differs from IFN-alphaAD(Bgl II) at just three residue positions, two of which reside in this critical domain: 69 (S/T), 80(T/D) and 86(Y/C). IFN-alphaAD(Pvu II) demonstrates considerably reduced antiviral activity on murine cells compared with IFN-alphaAD(Bgl II) yet comparable activity to IFN-alpha 2a, on human cells.

Sequence homology among the different Type 1 IFNs in conserved regions would suggest evolutionary significance. It is noteworthy that the amino-and carboxy-terminal domains that have been identified as critical, are highly conserved among the different molecular subtypes of Type 1 IFNs. Within the 29–35 and 123–140 regions are structural motifs that are consistent with receptor binding domains: loop structures that are predominantly hydrophilic and located at the surface of the molecule. Some variation in sequence homology is apparent in the 78–95 region. The critical epitopes for Type I IFN receptor recognition are associated with the residue clusters 29–35 and 130–140, for all species of Type I IFNs. These epitopes constitute the receptor binding domains and are likely located in close spacial proximity to one another in the folded IFN. The specificity of action of a particular Type I IFN is conferred by the recognition epitope 78–95.

The basis for the specificity of interaction of the 78–95 domain and its putative cognate binding molecule is unknown. Studies with human growth hormone have shown that receptor binding involves both receptor recognition, by an epitope on the growth hormone, and dimerization of receptors, facilitated through the interaction of a separate epitope on the growth hormone. By analogy, once an IFN-alpha molecule is bound to its receptor, mediated by the recognition epitopes 29–35 and 130–140, the 78–95 epitope in HuIFN-alpha may interact with another Type 1 receptor, effecting dimerization. Using the cross-linking agent disuccinimidyl suberate for analysis of affinity- labeled cellular IFN binding components, the inventor and a number of other groups have shown that IFN-receptor complexes of 80 kDa and 140–160 kDa can be separated by SDS-PAGE. The molecular weight of the predicted IFN-alpha receptor protein is 63 kDa and that of the majority of IFN-alphas is 20 kDa, thus, monomer (receptor-IFN) and dimerized-(receptor-IFN-receptor) complexes, may represent the 80 kDa and 40–160 kDa moieties that have been detected.

Figure 5:
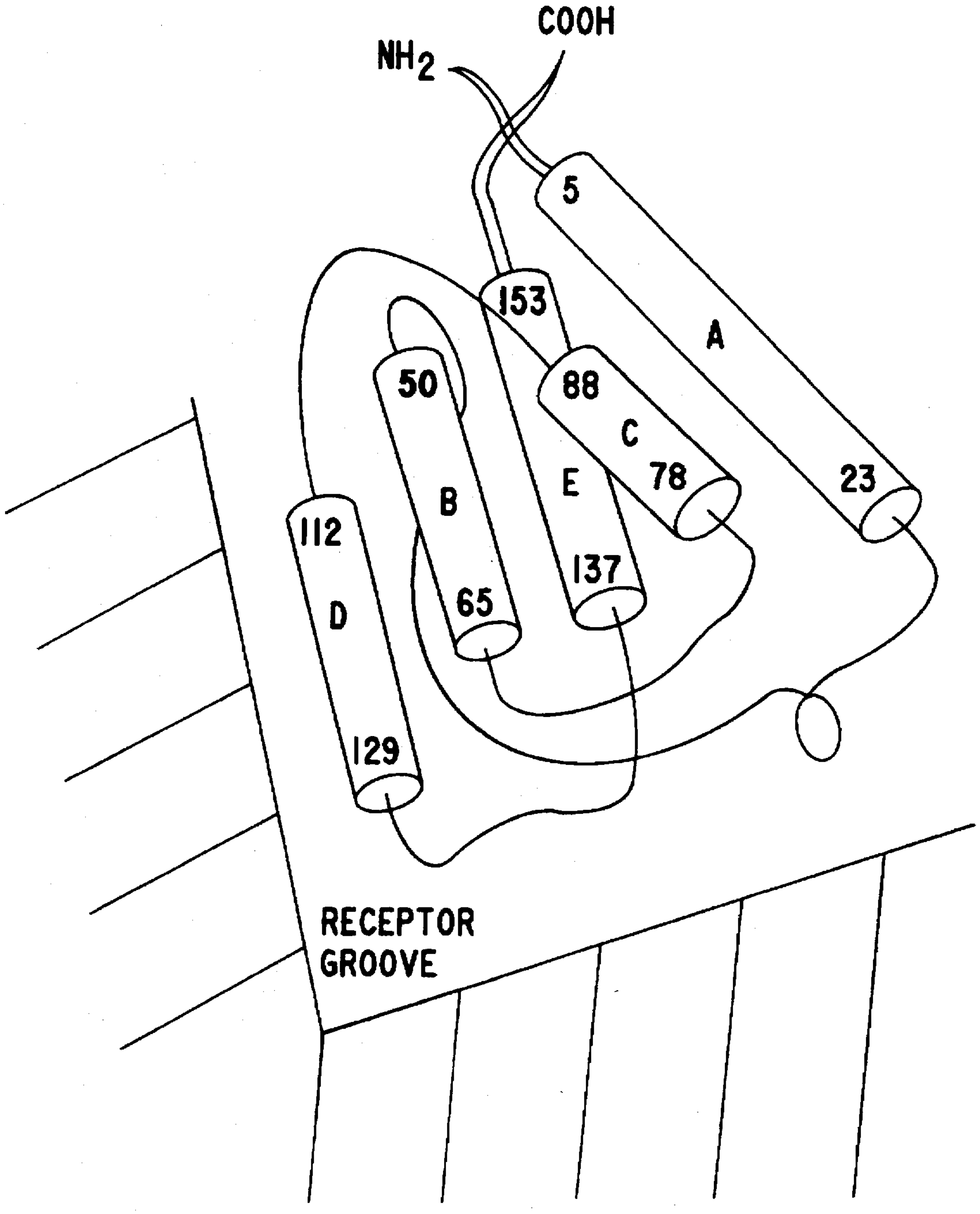
FIG. 5 is a representation of a model for the tertiary structure of Type 1 IFNs.

FIG. 5 illustrates a model for the tertiary structure of Type 1 IFNs. This model incorporates a helical bundle core, composed of the five helices A to E. The loop structures that constitute the proposed receptor recognition epitopes, residues 29–35 and 130–140, are shown as heavily shaded, broad lines and are aligned such that they dock in the receptor groove as shown. The third region implicated in the active conformation of the Type 1 IFNs, 78–95, is not buried in the receptor groove and is configured to allow binding to its cognate epitope on another Type 1 IFN receptor. The shaded areas in helices C and D represent residues that are critical for maintaining the correct structural presentation of the corresponding contiguous recognition epitopes. In agreement with a number of different models that have been proposed, the Type I IFNs are comprised predominantly of alpha-helical bundles that are packed together. The receptor recognition site is comprised of the AB loop, 29–35 and the D helix and DE loop, 123–140. These are aligned in such a way as to permit the IFN to bind to its receptor, in the receptor groove, such that the third epitope, 78–95, is exposed and not buried in the receptor groove. The initial interaction of the IFN molecule with the Type I IFN receptor would account for the abundant, low affinity receptor binding component, extrapolated from the Scatchard analyses of the different binding isotherms. The higher affinity component could be invoked once the IFN molecule is bound to its receptor. The heterogeneity of binding observed for IFN-alpha2a is absent in IFN-alpha$_1$Nδ4, and is explained by the alteration of the 29–35 and 78–95 epitopes in IFN-alpha$_1$Nδ4, as compared with IFN-alpha2a. This may lead to a reduction in signaling potential of the receptor-bound IFN and hence a reduction in biological potency.

There is some evidence to suggest that the proliferative state of a cell will determine whether the high affinity binding component is invoked on IFN-alpha2a binding to its receptor. Non-proliferating cells express fewer Type I IFN receptors and will not exhibit the characteristic heterogeneity of binding seen with proliferating cells. Interestingly, non-proliferating cells do possess both the 80 kDa and 140–160 kDa IFN-binding complexes. The data indicate that non-proliferating cells lack the high affinity component of IFN-alpha binding, that is not associated with IFN-receptor dimerization, yet may represent a secondary binding molecule. A comprehensive binding model, therefore, that would account for heterogeneity of binding distinct from receptor dimerization, would invoke the interaction of the IFN-bound receptor complex with a putative secondary binding molecule. The possibility that other accessory molecules are required for the full complement of IFN-receptor interactions, is supported by observations of high molecular weight complexes containing the IFN-alpha-receptor complex. Furthermore, the genetic transfer of the human IFN-alpha receptor into mouse cells, led to transfectants that exhibited a poor sensitivity to selected Type 1 human IFNs. These results infer that the transfected protein may not be sufficient for the complete binding activities of the IFNs. Indeed, in the receptor systems described for interleukin-6 and nerve growth factor, accessory proteins are required for the high affinity binding component of the receptor-ligand interaction. In the absence of experimental data, it cannot be discounted that the 78–95 epitope in Type 1 IFNs may interact with a species-specific secondary binding molecule. It is intriguing to suggest that the differential specificity of action that resides in IFN-alpha and IFN-beta, results from the specific interaction of the 78–95 region in the two IFNs with a complementary cognate accessory binding molecule. Moreover, the species specificity observed for the Type 1 IFNs may reside in the recognition of this species-specific cognate binding molecule, by the specific and variable 78–95 epitopes amongst the different Type 1 IFN species. The precedent for major determinants of specificity of interaction has been made with small nuclear ribonucleoproteins and specific RNAs: RNA binding specificity is conferred by short stretches of variant amino acid residues in two ribonucleoproteins that otherwise share extensive sequence homology. Certainly, among DNA binding proteins, exchange of amino acid residues between members of the helix-turn-helix and zinc finger protein families can result in the exchange of DNA binding specificity. The nature of the accessory binding molecule that may be associated with the Type 1 IFN receptor complex remains to be clarified.

I claim:

1. A novel IFN-receptor binding peptide having an amino acid sequence of the formula: CYS-LEU-LYS-ASP-ARG-HIS-ASP (SEQ. ID NO. 1).

2. A novel IFN-receptor binding peptide having an amino acid sequence of the formula: ASP-GLU-SER-LEU-LEU-GLU-LYS-PHE-TYR-THR-GLU-LEU-TYR-GLN-GLN-LEU-ASN-ASP (SEQ. ID NO. 2).

3. A novel IFN-receptor binding peptide having an amino acid sequence of the formula: ASN-GLU-THR-ILE-VAL-GLU-ASN-LEU-LEU-ALA-ASN-VAL-TYR-HIS-GLN-ILE-ASN-HIS (SEQ. ID NO. 3).

4. A novel IFN-receptor binding peptide having an amino acid sequence of the formula: TYR-LEU-THR-GLU-LYS-LYS-TYR-SER-PRO-CYS-ALA (SEQ. ID NO. 4).

5. A novel IFN-receptor binding peptide having an amino acid sequence of the formula: TYR-PHE-GLN-ARG-ILE-THR-LEU-TYR-LEU-THR-GLU-LYS-HYS-TYR-SER-PRO-CYS-ALA (SEQ. ID NO. 5).

6. A novel IFN-receptor binding peptide having an amino acid sequence of the formula: TYR-PHE-GLN-ARG-ILE-THR-LEU-TYR (SEQ. ID NO. 6).

7. A novel IFN-receptor binding peptide having an amino acid sequence of the formula: GLU-LEU-TYR-GLN-GLN-LEU-ASN-ASP (SEQ. ID NO. 7).

8. A polypeptide for use as an interferon-receptor binding peptide, said polypeptide selected from the group of peptides having an amino acid sequence of the formulae: CYS-LEU-LYS-ASP-ARG-HIS-ASP (SEQ. ID NO. 1); ASP-GLU-SER-LEU-LEU-GLU-LYS-PHE-TYR-THR-GLU-LEU-TYR-GLN-GLN-LEU-ASN-ASP (SEQ. ID NO. 2); ASN-GLU-THR-ILE-VAL-GLU-ASN-LEU-LEU-ALA-ASN-VAL-TYR-HIS-GLN-ILE-ASN-HIS (SEQ. ID NO. 3); TYR-LEU-THR-GLU-LYS-LYS-TYR-SER-PRO-CYS-ALA (SEQ. ID NO. 4); TYR-PHE-GLN-ARG-ILE-THR-LEU-TYR-LEU-THR-GLU-LYS-LYS-TYR-SER-PRO-CYS-ALA (SEQ. ID NO. 5); TYR-PHE-GLN-ARG-ILE-THR-LEU-TYR (SEQ. ID NO. 6); and GLU-LEU-TYR-GLN-GLN-LEU-ASN-ASP (SEQ. ID NO. 7).

* * * * *